United States Patent
Jansson et al.

(10) Patent No.: US 9,821,102 B2
(45) Date of Patent: *Nov. 21, 2017

(54) DIALYSIS PRECURSOR COMPOSITION

(75) Inventors: Olof Jansson, Vellinge (SE); Torbjorn Linden, Hasslo (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/128,130

(22) PCT Filed: Jun. 11, 2012

(86) PCT No.: PCT/EP2012/060969
§ 371 (c)(1),
(2), (4) Date: Mar. 18, 2014

(87) PCT Pub. No.: WO2012/175353
PCT Pub. Date: Dec. 27, 2012

(65) Prior Publication Data
US 2014/0377376 A1    Dec. 25, 2014

Related U.S. Application Data

(60) Provisional application No. 61/499,209, filed on Jun. 21, 2011.

(30) Foreign Application Priority Data

Jun. 20, 2011  (SE) ...................... 1150565

(51) Int. Cl.
| | |
|---|---|
| *A61M 1/16* | (2006.01) |
| *A61K 31/7004* | (2006.01) |
| *A61K 33/06* | (2006.01) |
| *A61K 33/14* | (2006.01) |
| *A61K 33/10* | (2006.01) |
| *A61K 31/19* | (2006.01) |
| *A61K 31/191* | (2006.01) |
| *A61K 31/194* | (2006.01) |
| *A61K 31/198* | (2006.01) |
| *A61K 31/366* | (2006.01) |
| *A61K 31/385* | (2006.01) |
| *A61J 1/05* | (2006.01) |

(52) U.S. Cl.
CPC .............. *A61M 1/1654* (2013.01); *A61J 1/05* (2013.01); *A61K 31/19* (2013.01); *A61K 31/191* (2013.01); *A61K 31/194* (2013.01); *A61K 31/198* (2013.01); *A61K 31/366* (2013.01); *A61K 31/385* (2013.01); *A61K 31/7004* (2013.01); *A61K 33/06* (2013.01); *A61K 33/10* (2013.01); *A61K 33/14* (2013.01); *A61M 1/1666* (2014.02)

(58) Field of Classification Search
CPC ........ A61K 33/06; A61K 33/14; A61K 33/10; A61K 31/385; A61K 31/198; A61K 31/366; A61K 31/191; A61K 31/194; A61K 31/19; A61K 31/7004; A61M 1/1654; A61M 1/1666; A61J 1/05
USPC .................................................. 424/717, 722
See application file for complete search history.

(56) References Cited

U.S. PATENT DOCUMENTS

| | | |
|---|---|---|
| 3,560,380 A | 2/1971 | Stade |
| 4,636,412 A | 1/1987 | Field |
| 4,756,838 A | 7/1988 | Veltman |
| 6,610,206 B1 | 8/2003 | Callan et al. |
| 9,029,333 B2 | 5/2015 | Sugiyama et al. |
| 2004/0019313 A1 | 1/2004 | Childers et al. |
| 2004/0057885 A1 | 3/2004 | Taylor |
| 2004/0060865 A1 | 4/2004 | Callan et al. |
| 2007/0087212 A1 | 4/2007 | Iyengar et al. |
| 2007/0231395 A1 | 10/2007 | Kai et al. |
| 2008/0015487 A1 | 1/2008 | Szamosfalvi et al. |
| 2009/0306002 A1 | 12/2009 | Nakanishi et al. |
| 2010/0120702 A1 | 5/2010 | Sugiyama et al. |
| 2011/0172583 A1 | 7/2011 | Callan et al. |
| 2012/0291875 A1 | 11/2012 | Shah et al. |

FOREIGN PATENT DOCUMENTS

| | | |
|---|---|---|
| CN | 1938058 A1 | 3/2007 |
| EP | 0 034 916 A1 | 9/1981 |
| EP | 0 399 918 | 11/1990 |
| EP | 0 417 478 A1 | 3/1991 |

(Continued)

OTHER PUBLICATIONS

Barry et al. (Basis for Using Moisture Vapor Transmission Rate Per Unit Product in the Evaluation of Moisture-Barrier Equivalence of Primary Packages for Solid Oral Dosage Forms, 2004).*
CurTec article (http://www.pharmaceutical-networking.com/moisture-resistant-packaging/) 2015.*
Nikhil Mehrotra (Masters Theses): A Study of Water Vapor Transmission Rate of Blister Packs by USP Standard and Continuous Gravimetric Protocol 2010.*
International Search Reported cited in PCT/EP2012/060969 dated Oct. 2, 2012.
Ahmad et al., "Dialysate Made From Dry Chemicals Using Citric Acid Increases Dialysis Dose," American Journal of Kidney Diseases, vol. 35, No. 3 (Mar.), 2000: pp. 493-499.
Gabutti et al., "Citrate- vs. acetate-based dialysate in bicarbonate haemodialysis: consequences on haemodynamics, coagulation, acid-base status, and electrolytes," BMC Nephrology 2009, 10:7.
Nilsson, "Citrate vs. Acetate in Bicarbonate-Based Dialysis Fluid— What Does it Mean Clinically?" Gambro Lundia AB, 2012.

(Continued)

*Primary Examiner* — Blessing M Fubara
(74) *Attorney, Agent, or Firm* — K&L Gates LLP

(57) ABSTRACT

The present invention concerns a dialysis acid precursor composition for use during preparation of a dialysis acid concentrate solution and for mixing with water, a sodium containing concentrate, and a bicarbonate containing concentrate into a ready-for-use dialysis solution. Said dialysis acid precursor composition consists of powder components comprising glucose, at least one dry acid and at least one calcium salt, and optionally potassium salt, and magnesium salt. According to the invention said glucose and said at least one calcium salt, are present as anhydrous components in said dialysis acid precursor composition.

14 Claims, No Drawings

(56) References Cited

FOREIGN PATENT DOCUMENTS

| | | | |
|---|---|---|---|
| EP | 0 602 014 A1 | 6/1994 | |
| EP | 0 602 921 A1 | 6/1994 | |
| EP | 1 059 083 A1 | 12/2000 | |
| EP | 1 101 483 A2 | 5/2001 | |
| EP | 1 192 961 A2 | 4/2002 | |
| EP | 1 714 657 A1 | 10/2006 | |
| EP | 1 731 183 A1 | * 12/2006 | |
| EP | 1834652 | 9/2007 | |
| EP | 2119438 | 11/2009 | |
| EP | 2123270 | 11/2009 | |
| EP | 2 151 247 A1 | 2/2010 | |
| EP | 2 286 820 A1 | 2/2011 | |
| FR | 2 766 797 A1 | 2/1999 | |
| JP | H02-311418 A | 12/1990 | |
| JP | H04-257522 A | 9/1992 | |
| JP | H10-87478 A | 4/1998 | |
| JP | 2003104869 | 4/2003 | |
| JP | 2004-283569 A | 10/2004 | |
| JP | 2005-206572 A | 8/2005 | |
| RU | 2006103497 A | 8/2007 | |
| TW | 200911287 A | 3/2009 | |
| WO | 92/11046 A1 | 7/1992 | |
| WO | 00/57935 A1 | 10/2000 | |
| WO | 01/21233 | 3/2001 | |
| WO | 03/043680 A1 | 5/2003 | |
| WO | 2005/002599 A1 | 1/2005 | |
| WO | 2005/094918 A1 | 10/2005 | |
| WO | 2010/055963 | 5/2010 | |
| WO | 2010/112547 A1 | 10/2010 | |
| WO | 2010/112570 A1 | 10/2010 | |
| WO | WO 2010/112547 A1 | * 10/2010 | |
| WO | WO 2010/112570 A1 | * 10/2010 | |
| WO | 2011/161055 A1 | 12/2011 | |
| WO | 2011/161056 A2 | 12/2011 | |
| WO | 2012/175353 A1 | 12/2012 | |
| WO | 2012/175354 A1 | 12/2012 | |
| WO | 2013/004362 A1 | 1/2013 | |

OTHER PUBLICATIONS

Gärtner, Heinz, "Developments in barrier films," Symposium "Sperrschichtfolien [Barrier films]" on Jun. 30/Jul. 1, 2004, Würzburg, Germany.
TW200911287 Application—Incomplete Translation—p. 1 is missing.
TW200911287—Translation of Office Action—8 pages.
Ing T.S. et al., Employing L-lactic acid powder in the preparation of a dry "acid concentrate" for use in a bicarbonate-based dialysis solution-generating system: experience in hemodialysis patients, The International journal of artificial organs 1994, vol. 17, nr 2, p. 70-73.
Japanese Office Action for Japanese Application No. 2013-515839, dated Jul. 28, 2015.
Sigma-Aldrich Product Spedification form for Calcium Chloride; downloaded Mar. 15, 2016.
Norner AS download showing WVTR calculation for: FEP layer (1-mm); downloaded Feb. 13, 2015.
Norner AS download showing WVTR calculation for: PMMA layer (1-mm); downloaded Feb. 14, 2015.
Norner AS download showing WVTR calculation for: PTFE layer (1-mm); downloaded Feb. 14, 2015.
Norner AS download showing WVTR calculation for: PTFE-PTFE dual-layer (1-mm); downloaded Feb. 14, 2015.
Norner AS download showing WVTR calculation for: PTFE layer (2-mm); downloaded Feb. 14, 2015.
Norner AS download showing WVTR calculation for: PVDC layer (1-mm); downloaded Feb. 13, 2015.
Norner AS download showing WVTR calculation for: PTFE-PMMA dual-layer (1-mm); downloaded Feb. 14, 2015.
Oracle Packaging; data for aluminum foil; downloaded Feb. 16, 2015.
International Search Report cited in PCT/EP2012/060971 dated Aug. 21, 2012.
Magnesium chloride 4.5 hydrate, European Pharmacopoeia 7.3 Jan. 2012.
International Preliminary Report on Patentability for International Application No. PCT/EP2012/075008, dated Jun. 24, 2014.
International Search Report for International Application No. PCT/EP2012/075008, dated Mar. 6, 2013.
Written Opinion of the International Searching Authority for International Application No. PCT/EP2012/075008, dated Mar. 6, 2013.
International Preliminary Report on Patentability for International Application No. PCT/EP2012/075007, dated Jun. 24, 2014.
International Search Report for International Application No. PCT/EP2012/075007, dated Mar. 6, 2013.
Written Opinion of the International Searching Authority for International Application No. PCT/EP2012/075007, dated Mar. 6, 2013.
Search Report for related International Patent Application No. PCT/EP2013/054386 dated May 23, 2013 (6 pages).
Written Opinion for related International Patent Application No. PCT/EP2013/054386 dated May 23, 2013 (5 pages).
Gambro Lundia AB's Response to Opposition filed in related European patent application No. 11729087.4 on Aug. 5, 2016.
Kipouros et al., "A Thermal Analysis of the Production of Anhydrous MgCl2," Journal of Light Metals, May 2001 (cited in Response to Opposition filed in related European patent application No. 11729087.4 on Aug. 5, 2016).
Declaration of David Karlsson relating to film thickness, dated Jul. 29, 2016 (cited in Response to Opposition filed in related European patent application No. 11729087.4 on Aug. 5, 2016).
Annex A (curriculum vitae) of David Karlsson Declaration (annex to reference cited in Response to Opposition filed in related European patent application No. 11729087.4 on Aug. 5, 2016).
Translation Declaration signed by Don Sanderson on Jul. 22, 2016 attesting to the translation of selected paragraphs of JP 10-87478 (cited by opponent Fresenius Medical Care), (cited in Response to Opposition filed in related European patent application No. 11729087.4 on Aug. 5, 2016).
Experimental annex providing stability data (cited in Response to Opposition filed in related European patent application No. 11729087.4 on Aug. 5, 2016).
Notice of Opposition filed in related European Patent case No. 11729087.4-1453 / 2585076 by Fresenius Medical Care AG & Co. KGaA on Dec. 3, 2015 (16 pages).
Vortrag Dr. Gärtner mit dem Titel, "Entwicklungen bei Sperrschichtfolien", ("Fachtagung, Sperrschichtfolien" vom 30. Jun./Jul. 1, 2004 in Wurzburg) nebst eidesstattlicher Versicherung des Hernn Dietmar Hansel (cited in Notice of Opposition filed in related European patent application No. case No. 11729087.4-1453 / 2585076 by Fresenius Medical Care AG & Co. KGaA on Dec. 3, 2015) (35 pages).
Summons to attend oral proceedings pursuant to Rule 115(1) EPC issued in related European Patent case No. 11729087.4-1453 / 2585076 dated Aug. 30, 2016 (9 pages).
Observations (Experimental Data) filed in related European patent application No. case No. 11729087.4-1453 / 2585076 by Gambro Lundia AB on Aug. 5, 2016 (5 pages).
Declaration of Ola Carlsson filed in related European patent application No. case No. 11729087.4-1453 / 2585076 by Gambro Lundia AB on Aug. 5, 2016 (13 pages).
English translation of Japanese Office Action dated Nov. 22, 2016 in corresponding Japanese application No. 2014-560335 (4 pages).
English translation of Korean Office Action dated May 22, 2017 in corresponding Korean application No. 10-2013-7001784 (8 pages).

* cited by examiner

DIALYSIS PRECURSOR COMPOSITION

CROSS RELATED APPLICATION

This application is the U.S. national phase of International Application No. PCT/EP2012/060969 filed 11 Jun. 2012 which designated the U.S. and claims priority to U.S. Patent Application Ser. No. 61/499,209 filed 21 Jun. 2011 and Swedish Patent Application No. 1150565-8 filed 20 Jun. 2011, the entire contents of all of which applications are hereby incorporated by reference.

TECHNICAL FIELD

The present invention concerns a dialysis acid precursor composition for use during preparation of a dialysis acid concentrate solution and for further mixing with water, a sodium containing concentrate, and a bicarbonate containing concentrate into a ready-for-use dialysis solution. The present invention further concerns a method of providing a dialysis acid concentrate solution for dilution with water, a sodium containing concentrate, and a bicarbonate containing concentrate to produce a ready-for-use dialysis solution. Even further, the present invention concerns use of said dialysis acid precursor composition for preparation of a dialysis acid concentrate solution, for preparing a dialysis solution, an infusion solution, a replacement solution, a rinsing solution or a priming solution.

BACKGROUND

When a person's kidney does not function properly uremia is developed. Dialysis is a well established treatment technique for uremia. Essentially, dialysis artificially replaces the functions of the kidney. There are two distinct types of dialysis; hemodialysis and peritoneal dialysis.

Hemodialysis involves withdrawing blood from the body and cleaning it in an extracorporeal blood circuit and then returning the cleansed blood to the body. The extracorporeal blood circuit includes a dialyzer which comprises a semipermeable membrane. The semipermeable membrane has a blood side and a dialysate side. Waste substances and excess fluid is removed from the blood (passing on the blood side of the semipermeable membrane) through the semipermeable membrane over to the dialysate side of the semipermeable membrane.

Hemodialysis may be performed in three different treatment modes; hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis solution is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis solution, through the semipermeable membrane and into the blood.

In hemofiltration, no dialysis solution is brought in contact with the dialysate side of the semipermeable membrane. Instead only a transmembrane pressure is applied over the semipermeable membrane thereby removing fluid and waste substances from the blood through the semipermeable membrane wall and into the dialysate side thereof (convective flow). Fluid and waste substances are then passed to drain. To replace some of the removed fluid, a correctly balanced electrolyte/buffer dialysis solution (also named infusion fluid or replacement fluid) is infused into the extracorporeal blood circuit. This infusion may be done either pre the dialyzer (pre-infusion mode) or post the dialyzer (post-infusion mode) or both.

Hemodiafiltration is a combination of hemodialysis and hemofiltration, a treatment mode that combines transport of waste substances and excess fluids through the semipermeable membrane wall by both diffusion and convection. Thus, here a dialysis solution is brought in contact with the dialysate side of the semipermeable membrane in a continuously flowing manner, and a dialysis solution (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible. When home dialysis is performed the patient is free to perform dialysis more frequently and also in a more gentle treatment with longer duration, i.e. 4-8 hours per treatment and 5-7 treatments per week. The dose and treatment duration may be adjusted to each patient's demands and needs.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patient's status. Also here the removal of waste substances and excess fluid from the patient is effected by any or a combination of the treatment modes hemodialysis, hemofiltration and hemodiafiltration.

In a peritoneal dialysis treatment a hypertonic dialysis solution is infused into the peritoneal cavity of the patient. In this treatment solutes and water is exchanged in the capillary vessels of a patient's peritoneal membrane with said hypertonic dialysis solution. The principle of this method is diffusion of solutes transferred according to the concentration gradient and water migration due to the osmotic differences over the peritoneal membrane.

The dialysis solutions used in all the above dialysis techniques contain mainly electrolytes like sodium, magnesium, calcium, potassium, an acid/base buffer system and optionally glucose or a glucose-like compound. All the components in dialysis solutions are selected to control the levels of electrolytes and the acid-base equilibrium within the blood and to remove waste materials from the blood.

Dialysis solutions are today prepared from different types of concentrates. It may be liquid concentrates of different degree of concentration, where the acid/electrolyte part is separated from the buffer part. It may be provided in highly concentrated volumes of 1-8 L in bags for bedside use, or in more diluted concentrated volumes of 5-20 L in canisters, which still are for bedside use. Concentrates may also be prepared in central tanks in volumes of 300-1000 L.

When using bicarbonate as a buffer component in the dialysis solution, bicarbonate is often provided as a dry concentrate for on-line-preparation of saturated bicarbonate containing concentrate. The saturated bicarbonate containing concentrate is thereafter mixed with an acid/electrolyte concentrate and further diluted with purified water to produce the on-line prepared dialysis solution.

Dialysis solutions have improved in quality over the years, and the availability of concentrated precursor compositions for further dilution and mixing with other components into a ready-for-use dialysis solution have decreased the costs and improved the environmental issues.

One way to further limit the costs and improve the environmental issues would be to provide a dialysis precursor composition in which all components are dry. However, having all components as dry components adds new problems.

Firstly, dry acid and bicarbonate powder are not compatible. When a small amount of humidity is present, bicarbonate will break down to carbon dioxide.

Secondly, magnesium chloride and calcium chloride mixed with bicarbonate will provide areas were the solubility product of calcium carbonate and/or magnesium carbonate will be exceeded which would cause precipitation thereof when water is added during preparation of a concentrate or a dialysis solution.

Thirdly, even if bicarbonate is excluded to a separate cartridge, still problems would be experienced. E.g. caking and lump formation of the different components will render the dissolution thereof more difficult or even impossible when preparing the ready-for-use dialysis solution.

Fourthly, if glucose is present, a discoloration of the precursor, and later on, the ready-for-use dialysis solution would arise as a result of glucose degradation products, which should be avoided due to toxicity and limits set by authority regulations, e.g. European Pharmacopeia.

All the problems above are due to the presence of humidity within the dry precursor compositions.

In prior art this has been solved by preparing granulates of the different components and creating different layers of the different components within each granulate, like disclosed in EP0567452 or EP1714657.

However, this still may give rise to interactions between the different layers, and it is also a time-consuming matter of providing a completely and properly dissolved granulate for the preparation of the ready-for-use dialysis solution. Further, it is difficult to ensure proper composition and concentration of the different components both within the granulate and thus also within the finally prepared ready-for-use dialysis solution.

SUMMARY OF THE INVENTION

One object of the present invention is to provide a dialysis precursor composition which show further improved stability, limited chemical degradation and increased shelf life.

Another object of the present invention is to provide a dialysis precursor composition which give rise to further cost savings and further improved environmental benefits.

These objects are achieved, in full or at least in part, by a dialysis acid precursor composition according to claim 1, with different embodiments defined by dependent claims 2-6.

These objects are also achieved, in full or at least in part, by a method according to claim 7, and a use of the dialysis acid precursor composition according to claims 8 and 9.

The present invention concerns a dialysis acid precursor composition for use during preparation of a dialysis acid concentrate solution and for further mixing with water, a sodium containing concentrate, and a bicarbonate containing concentrate into a ready-for-use dialysis solution. Said dialysis acid precursor composition consists of powder components comprising glucose, at least one dry acid and at least one calcium salt, and optionally potassium salt, and magnesium salt. According to the invention said glucose and said at least one calcium salt are present as anhydrous components in said dialysis acid precursor composition. Further, said dialysis acid precursor composition is sealed in a moisture-resistant container with a water vapour transmission rate less than 0.3 $g/m^2/d$ at 38° C./90% RH.

The present invention further concerns a method of providing a dialysis acid concentrate solution for dilution with water, a sodium containing concentrate, and a bicarbonate containing concentrate to produce a ready-for-use dialysis solution. According to the invention this method comprises:

(a) providing a dialysis precursor composition comprising glucose, at least one dry acid, and at least one calcium salt, optionally potassium salt, and magnesium salt, wherein said glucose and said at least one calcium salt are present as anhydrous components in said dialysis acid precursor composition, (b) providing said dialysis precursor composition in a sealed, moisture-resistant container with a water vapour transmission rate less than 0.3 $g/m^2/d$ at 38° C./90% RH, and (c) adding a prescribed volume of water to said dialysis precursor composition in said container and mixing thereof, thereby providing said dialysis acid concentrate as a solution.

The present invention further concerns use of said dialysis acid precursor composition for preparing a dialysis acid concentrate solution.

Finally, the present invention concerns use of said dialysis acid precursor composition for preparing a dialysis solution, an infusion solution, a replacement solution, a rinsing solution or a priming solution.

Other embodiments of the present invention are evident from the description below and the dependent claims.

DETAILED DESCRIPTION OF THE INVENTION

A wide variety of different combinations and partitions of dry powder components of normal dialysis solutions like potassium chloride, magnesium chloride, calcium chloride, glucose, sodium chloride, sodium bicarbonate, dry acids like citric acid, glucono-δ-lactone, etc. were prepared and put in a forced stability study. Matters like caking, lump formation, discoloration and dissolution rate were investigated after 1 month, 4 months and 10 months storage time.

It was identified that, as expected earlier, sodium bicarbonate needs to be separated from the other components due to carbon dioxide formation, calcium carbonate precipitation, and magnesium carbonate precipitation. However, when combining the remaining components of a normal dialysis solution the crystalline water attached to glucose and calcium chloride caused problems with caking and lump formation within the powder compositions and discoloration of glucose. By replacing glucose with anhydrous glucose and by replacing calcium chloride dihydrate with anhydrous calcium chloride, or another calcium salt not containing any crystalline water, the powder composition remained stable, free flowing and no discoloration evolved. Thus, in order to make sure that a stable composition is provided the container material used for storing the composition should be moisture-resistant and not allow passage of an amount equal to or above the amount which equals the crystalline water normally attached with the calcium salt. This is achieved with a container material having a water vapour transmission rate less than 0.3 $g/m^2/d$ at 38° C./90% RH.

In another embodiment said container material has a water vapour transmission rate less than 0.2 g/m²/d at 38° C./90% RH.

In another embodiment said container material has a water vapour transmission rate between 0.05-0.3 g/m²/d at 38° C./90% RH.

In even another embodiment said container material has a water vapour transmission rate between 0.05-0.2 g/m²/d at 38° C./90% RH. In another embodiment said container material has a water vapour transmission rate between 0.1-0.3 g/m²/d at 38° C./90% RH.

In even another embodiment said container material has a water vapour transmission rate between 0.1-0.2 g/m²/d at 38° C./90% RH.

According to the invention said dialysis acid precursor composition consists of powder components comprising glucose, at least one dry acid and at least one calcium salt, and optionally potassium salt, and magnesium salt, wherein said glucose and said at least one calcium salt are present as anhydrous components in said dialysis acid precursor composition within the moisture-resistant container.

In other embodiments of the present invention said at least one dry acid is selected from the group comprising lactic acid, citric acid, gluconic acid, glucono-δ-lactone, N-acetyl cystein and α-lipoic acid. Thus, a combination of dry acids may be used within said dialysis acid precursor composition, and by providing a combination of different dry acids, other functions and effects, in addition to said acidic function, may be provided, like for instance antioxidative effects (as with gluconic acid, glucono-δ-lactone, N-acetyl cystein and α-lipoic acid), anticoagulation effects (as with citric acid) and so forth.

In even further embodiments said at least one calcium salt in said dialysis acid precursor composition, is selected from the group comprising anhydrous calcium chloride, calcium gluconate, calcium citrate (tricalcium dicitrate), calcium lactate, and calcium α-ketoglutarate. Also here a combination of different calcium salts may be used in order to tailor specific add-on features, like antioxidative effects from calcium gluconate, or anticoagulation effects from calcium citrate, and so forth.

In one embodiment said at least one calcium salt in said dialysis acid precursor composition comprises anhydrous calcium chloride. By using anhydrous calcium chloride in a dry dialysis acid precursor composition, the anhydrous component will act as desiccant if any water would transport into the bag.

In one embodiment said at least one calcium salt in said dialysis acid precursor composition is selected from the group consisting of calcium gluconate, calcium citrate and calcium lactate.

In other embodiments, in which magnesium salt is present, said magnesium salt in said dialysis acid precursor composition, is at least one chosen from the group comprising magnesium chloride with different degree of hydration, e.g. magnesium chloride hexahydrate or magnesium chloride dihydrate. In one embodiment said dialysis precursor composition is provided in a specific amount and is configured to be mixed with a prescribed volume of water within said moisture-resistant container to provide a dialysis acid concentrate solution. Thus, said moisture-resistant container is configured to receive and dispense solutions up to said prescribed volume.

In one embodiment said prescribed volume may be within the range of from 0.3 to 8 L.

In another embodiment said prescribed volume may be within the range of from 5-20 L.

In even another embodiment said prescribed volume may be within the range of 300-1000 L.

Further, in one embodiment said dialysis acid concentrate solution is configured and provided to be diluted within the range of 1:30 to 1:200 with water, a sodium containing concentrate, and a bicarbonate containing concentrate.

The present invention further concerns a method of providing a dialysis acid concentrate solution. Said dialysis acid concentrate solution is further intended to be mixed with additional water, a sodium containing concentrate, and a bicarbonate containing concentrate to provide a ready-for-use dialysis solution. According to the invention said method comprises (a) providing a dialysis precursor composition comprising glucose, at least one dry acid, and at least one calcium salt, optionally potassium salt, and magnesium salt, wherein said glucose and said at least one calcium salt are present as anhydrous components in said dialysis acid precursor composition, (b) providing said dialysis precursor composition in a sealed, moisture-resistant container with a water vapour transmission rate less than 0.3 g/m²/d at 38° C./90% RH, and (c) adding a prescribed volume of water to said dialysis precursor composition in said container and mixing thereof, thereby providing said dialysis acid concentrate as a solution.

Glucose is provided in such a quantity in said moisture-resistant container that a concentration of 30-400 g/L is provided in the dialysis acid concentrate solution when a prescribed volume of water has entered into said moisture-resistant container.

Said dry acid is provided in such a quantity in said moisture-resistant container that a concentration within the range of 60-800 mEq/L H⁺ (acid) is provided in the dialysis acid concentrate solution when a prescribed volume of water has entered into said moisture-resistant container.

Further, said at least one calcium salt is provided in such a quantity in said moisture-resistant container that a concentration within the range of 30-500 mM calcium ions is provided in the dialysis acid concentrate solution when a prescribed volume of water has entered into said moisture-resistant container.

If present, said magnesium salt is provided in such a quantity in said moisture-resistant container that a concentration within the range of 7.5-150 mM magnesium ions is provided in the dialysis acid concentrate solution when a prescribed volume of water has entered into said moisture-resistant container.

If present, potassium salt is provided in such a quantity in said moisture-resistant container that a concentration within the range of 0-800 mM potassium ions is provided in the dialysis acid concentrate solution when a prescribed volume of water has entered into said moisture-resistant container.

In one embodiment said dry dialysis acid precursor composition comprises the different components in such an amount that, when said dry dialysis acid precursor composition has been dissolved and mixed with water, a sodium concentrate, and a bicarbonate concentrate, it provides a ready-for-use dialysis solution comprising from about 130-150 mM of sodium ions, from about 0 to 4 mM of potassium ions, from about 1-2.5 mM of calcium ions, from about 0.25 to 1 mM of magnesium ions, from about 0 to 2% (g/l) glucose from about 85 to 134 mM chloride ions, from about 2 to 4 mEq/L acid, and from about 25 to 45 mEq/L bicarbonate ions.

Thus, the present invention provides a prepackaged container with a dry dialysis acid precursor composition for use during preparation of a dialysis acid concentrate solution and for mixing with water, a sodium containing concentrate, and a bicarbonate containing concentrate into a ready-for-use dialysis solution, wherein said dialysis acid precursor composition consists of powder components comprising glucose, at least one dry acid and at least one calcium salt. Optionally said dialysis acid precursor composition further comprises potassium salts, and magnesium salts. According to the invention said glucose and said at least one calcium salt is present as anhydrous component in said dialysis acid precursor composition and said dialysis acid precursor composition is sealed in a moisture-proof container with a water vapour transmission rate less than 0.3 $g/m^2/d$ at 38° C./90% RH.

EXAMPLES

By way of example, and not limitation, the following examples identify a variety of dialysis acid precursor compositions pursuant to embodiments of the present invention.

In examples 1-4, the tables show the content of dialysis acid precursor compositions for dilution 1:35. The prescribed volume of each dialysis acid concentrate solution (DACS in tables below) is 5.714 L, and the final volume of each ready-for-use dialysis solution (RFUDS in tables below) is 200 L.

Example 1

| Ingredient | Amount (g) | Conc in DACS (mM) | Conc in RFUDS (mM) |
|---|---|---|---|
| Potassium chloride | 29.81 | 70 | 2 |
| Magnesium chloride hexahydrate | 20.33 | 17.5 | 0.5 |
| Calcium gluconate | 129.1 | 52.5 | 1.5 |
| Citric acid | 38.42 | 35 | 1 |
| Glucose anhydrous | 200 | 194 | 5.55 |

Example 2

| Ingredient | Amount (g) | Conc in DACS (mM) | Conc in RFUDS (mM) |
|---|---|---|---|
| Magnesium chloride hexahydrate | 20.33 | 17.5 | 0.5 |
| Calcium gluconate | 129.1 | 52.5 | 1.5 |
| Citric acid | 38.42 | 35 | 1 |
| Glucose anhydrous | 400 | 388.8 | 11.11 |

Example 3

| Ingredient | Amount (g) | Conc in DACS (mM) | Conc in RFUDS (mM) |
|---|---|---|---|
| Potassium chloride | 29.81 | 70 | 2 |
| Magnesium chloride hexahydrate | 20.33 | 17.5 | 0.5 |
| Calcium chloride anhydrous | 33.30 | 52.5 | 1.5 |
| Glucono-delta-lactone | 142.5 | 140 | 4 |
| Glucose anhydrous | 200 | 194 | 5.55 |

Example 4

| Ingredient | Amount (g) | Conc in DACS (mM) | Conc in RFUDS (mM) |
|---|---|---|---|
| Potassium chloride | 29.81 | 70 | 2 |
| Magnesium chloride hexahydrate | 20.33 | 17.5 | 0.5 |
| Calcium chloride anhydrous | 33.30 | 52.5 | 1.5 |
| Citric acid | 38.42 | 35 | 1 |
| Glucose anhydrous | 200 | 194 | 5.55 |

In examples 5 and 6, the tables show the content of a dry acid precursor composition for dilution 1:200. The prescribed volume of each dialysis acid concentrate solution (DACS in tables below) is 1 L, and the final volume of each ready-for-use dialysis solution (RFUDS in tables below) is 200 L.

Example 5

| Ingredient | Amount (g) | Conc in DACS (mM) | Conc in RFUDS (mM) |
|---|---|---|---|
| Magnesium chloride hexahydrate | 20.33 | 100 | 0.5 |
| Calcium gluconate | 150.6 | 350 | 1.75 |
| Citric acid | 38.42 | 200 | 1 |
| Glucose anhydrous | 200 | 1110 | 5.55 |

Example 6

| Ingredient | Amount (g) | Conc in DACS (mM) | Conc in RFUDS (mM) |
|---|---|---|---|
| Potassium chloride | 59.64 | 800 | 4 |
| Magnesium chloride hexahydrate | 20.33 | 100 | 0.5 |
| Calcium chloride anhydrous | 22.22 | 200 | 1 |
| Citric acid | 38.42 | 200 | 1 |
| Glucose anhydrous | 200 | 1110 | 5.55 |

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

The invention claimed is:

1. A dialysis acid precursor composition for use during preparation of a dialysis acid concentrate solution and for mixing with water, a sodium containing concentrate, and a bicarbonate containing concentrate into a ready-for-use dialysis solution, the dialysis acid precursor composition consisting of:

powder components comprising a glucose powder, at least one dry acid powder, a calcium chloride powder, and a hydrated magnesium chloride powder selected from the group consisting of a magnesium chloride hexahydrate powder and a magnesium chloride dihydrate powder, wherein the glucose powder and the calcium chloride powder are present as anhydrous components in the dialysis acid precursor composition, wherein the calcium chloride is in a quantity such that a concentration of 30-500 mM calcium ions is provided in the dialysis acid concentrate solution, and wherein the dialysis acid precursor composition is sealed in a moisture-resistant container with a water vapour transmission rate less than 0.3 g/m2/d at 38° C./90% RH.

2. A dialysis precursor composition according to claim 1, wherein said at least one dry acid is selected from the group comprising lactic acid, citric acid, gluconic acid, glucono-δ-lactone, N-acetyl cystein and α-lipoic acid.

3. A dialysis precursor composition according to claim 1, wherein said moisture-resistant container has a water vapour transmission rate of less than 0.2 g/m2/d at 38° C./90% RH.

4. A dialysis precursor composition according to claim 1, wherein said moisture-resistant container has a water vapour transmission rate of more than 0.05 g/m2/d at 38° C./90% RH.

5. A dialysis precursor composition according to claim 1, wherein said dialysis precursor composition is configured to be mixed with a prescribed volume of water within said moisture-resistant container to provide a dialysis acid concentrate solution.

6. The dialysis acid precursor composition of claim 1 wherein the powder components further comprise a potassium salt.

7. The dialysis precursor acid composition according to claim 1, wherein the powder components consist of the glucose powder, the at least one dry acid powder, the calcium chloride powder, the hydrated magnesium chloride powder, and a potassium salt, wherein the glucose powder and the calcium chloride powder are present as anhydrous components.

8. A method of providing a dialysis acid concentrate solution for dilution with water, a sodium containing concentrate, and a bicarbonate containing concentrate to produce a ready-for-use dialysis solution, the method comprising:
(a) providing a dialysis precursor composition comprising a glucose powder, at least one dry acid powder, a calcium chloride powder, and a hydrated magnesium chloride powder selected from the group consisting of a magnesium chloride hexahydrate powder and a magnesium chloride dihydrate powder, wherein the glucose powder and the calcium chloride powder are present as anhydrous components in the dialysis acid precursor composition,
(b) providing the dialysis precursor composition in a sealed, moisture-resistant container with a water vapour transmission rate less than 0.3 g/m2/d at 38° C./90% RH, and
(c) adding a prescribed volume of water to the dialysis precursor composition in the container and mixing thereof, thereby providing the dialysis acid concentrate solution, wherein the calcium chloride is in a quantity such that a concentration of 30-500 mM calcium ions is provided in the dialysis acid concentrate solution.

9. The method of claim 8 further comprising using the dialysis acid precursor composition to prepare at least one of a dialysis solution, an infusion solution, a replacement solution, a rinsing solution and a priming solution.

10. The method of claim 8 wherein the dialysis precursor composition includes a potassium salt.

11. The method of claim 8, wherein the dialysis precursor composition consist of the glucose powder, the at least one dry acid powder, the calcium chloride powder, the hydrated magnesium chloride powder, and a potassium salt, wherein the glucose powder and the calcium chloride powder are present as anhydrous components.

12. A method using a dialysis acid concentrate solution, the method comprising:
providing a dialysis precursor composition comprising an anhydrous glucose powder, a dry acid powder, an anhydrous calcium chloride powder, and a hydrated magnesium chloride powder selected from the group consisting of a magnesium chloride hexahydrate powder and a magnesium chloride dihydrate powder;
sealing the dialysis precursor in a moisture-resistant container having a water vapor transmission rate less than 0.3 g/m2/d at 38° C./90% RH; and
adding a prescribed amount of water to the dialysis precursor composition in the container to form a dialysis acid concentrate solution, wherein the calcium chloride is in a quantity such that a concentration of 30-500 mM calcium ions is provided in the dialysis acid concentrate solution.

13. The method of claim 12 comprising diluting the dialysis acid concentrate solution with at least one of a sodium containing concentrate and a bicarbonate containing concentrate to produce a ready-for-use dialysis solution.

14. The method of claim 12, wherein the dialysis precursor composition consist of the anhydrous glucose powder, the dry acid powder, the anhydrous calcium chloride powder, the hydrated magnesium chloride powder, and a potassium salt.

* * * * *